US00PP36504P2

(12) United States Plant Patent
Kleinwee

(10) Patent No.: US PP36,504 P2
(45) Date of Patent: Feb. 25, 2025

(54) ***PETUNIA* PLANT NAMED 'PEHY0082'**

(50) Latin Name: *Petunia hybrida*
Varietal Denomination: PEHY0082

(71) Applicant: SYNGENTA CROP PROTECTION AG, Basel (CH)

(72) Inventor: Theodorus Cornelis Maria Van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/445,435

(22) Filed: Aug. 14, 2023

(51) Int. Cl.
*A01H 5/02* (2018.01)
*A01H 6/82* (2018.01)

(52) U.S. Cl.
USPC ..... Plt./356.22

(58) Field of Classification Search
USPC ..... Plt./356.22
CPC . A01H 5/02; A01H 5/00; A01H 6/824; A01H 6/82
See application file for complete search history.

(56) References Cited

PUBLICATIONS

Ball Seed Itsy Pink *Petunia*, retrieved on Nov. 1, 2023 at https://www.ballseed.com/PlantInfo/?phid=048809068004054, 2 pp. (Year: 2023).*
Premier Color Nursery 2023 Master Availability, retrieved on Nov. 1, 2023 at https://s6r2y5.media.zestyio.com/2023-SPRING-MASTER-AVAIL_FINAL_web.pdf, 2 cover pages, 29, 2 back pages. (Year: 2023).*
Upov Pluto Nov. 1, 2023 retrieved on Nov. 1, 2023 at https://pluto.upov.int/result, one page. (Year: 2023).*
Ball Seed Itsy Pink Petunis retrieved online at https://www.ballseed.com/PlantInfo/?phid=048809068004054, 2 pp. (Year: 2023).*
CPVO Register S2/S3, Version 4.16.13, retrieved on Apr. 2, 2024 at https://online.plantvarieties.eu/publicConsultationDetails?registerId=20232071&denomination=pehy0082, 2 pp. (Year: 2024).*
Machovina Countdown to CAST 2023—Part 2 GPN Culture Connection retrieved on Apr. 3, 2024 at https://gpnmag.com/email/february-22-2023-culture-connection/, 3 pp. (Year: 2023).*
Premier Color Nursery 2023 Spring Master Avail retrieved online at https://s6r2y5.media.zestyio.com/2023-SPRING-MASTER-AVAIL_FINAL_web.pdf, 2 cover pages, 29, 2 back pages. (Year: 2023).*
Lucas Greenhouses *Petunia hybrida* Sanguna Sweet Pink retrieved on Nov. 13, 2024 at https://www.lucasgreenhouses.com/plant/Petunia-hybrida-Sanguna-Sweet-Pink, 3 pp. (Year: 2024).*

* cited by examiner

*Primary Examiner* — June Hwu
(74) *Attorney, Agent, or Firm* — Dale Skalla

(57) ABSTRACT

A new *Petunia* plant named 'PEHY0082' particularly distinguished by its very small flowers, a light pink flower color, medium early flowering and a semi trailing plant habit.

1 Drawing Sheet

Latin name of the genus and species of the plant claimed: *Petunia hybrida.*

Varietal denomination: 'PEHY0082'.

BACKGROUND OF THE NEW PLANT

The present invention comprises a new *Petunia*, botanically known as *Petunia hybrida*, and hereinafter referred to by the variety name 'PEHY0082'.

'PEHY0082' is a product of a planned breeding program. The new cultivar has very small flowers, a light pink flower color, medium early flowering and a semi trailing plant habit.

'PEHY0082' originated from a hybridization made in June 2019 in a controlled breeding environment in Enkhuizen, The Netherlands. The female parent was the proprietary selection 'PETBD1770-1V'. Compared to 'PEHY0082', it is less vigorous, has a dark purple flower color, is earlier flowering and has a more mounding to upright plant habit.

The male parent of 'PEHY0082' was the variety 'Itsy Magenta' ('PEHY0050', U.S. Plant Pat. No. 33,747); a plant with very small flowers, purple flower color, somewhat less vigorous and with a similar plant habit.

The resulting seeds were sown in September 2019. 'PEHY0082' was selected as one flowering plant within the progeny of the stated cross in November 2019 in a controlled environment in Enkhuizen, The Netherlands.

The first act of asexual reproduction of 'PEHY0082' was accomplished when vegetative cuttings were propagated from the initial selection in January 2020 in a controlled environment in Enkhuizen, The Netherlands.

BRIEF SUMMARY OF INVENTION

Horticultural examination of plants grown from cuttings of the plant initiated in January 2020 and continuing thereafter, has demonstrated that the combination of characteristics as herein disclosed for 'PEHY0082' are firmly fixed and are retained through successive generations of asexual reproduction.

'PEHY0082' has not been observed under all possible environmental conditions. The phenotype may vary significantly with variations in environment such as temperature, light intensity, and day length.

A Plant Breeder's Rights for this cultivar was applied for in Canada on Sep. 20, 2023, No. 23-11487. 'PEHY0082' has not been made publicly available prior to the effective filing date of this application, notwithstanding any disclosure that may have been made less than one year prior to the effective filing date of this application by the inventor or another who obtained 'PEHY0082' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0082' with colors being as true as possible with an illustration of this type.

Figure 1:
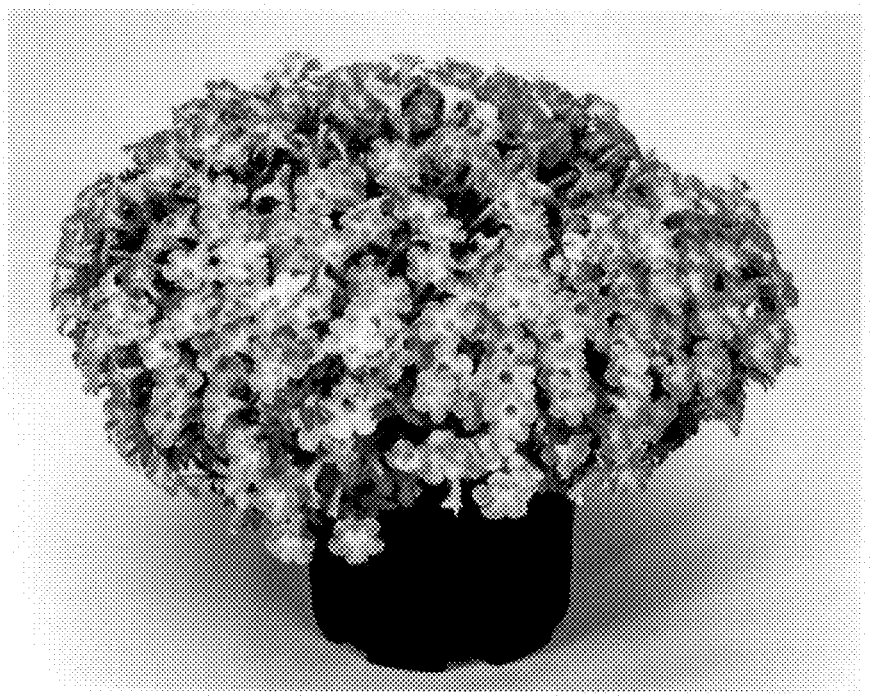
Figure 2:
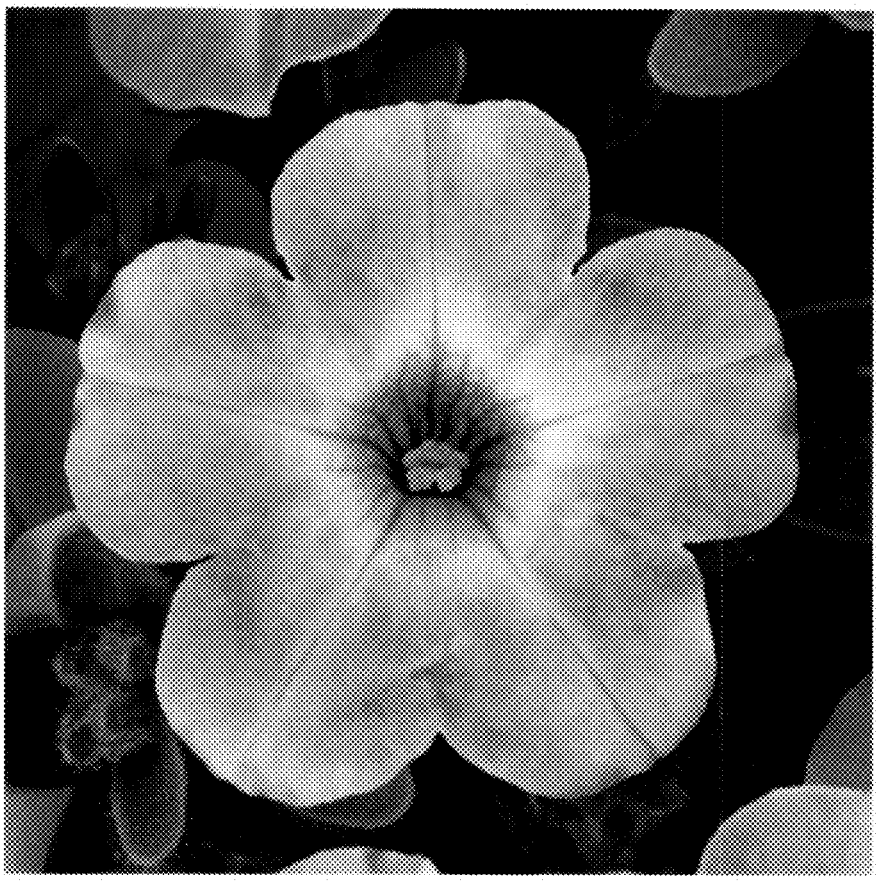

The photographic drawings show in FIG. 1 a flowering plant of the new variety and in FIG. 2 a close-up of the flowers.

DETAILED BOTANICAL DESCRIPTION

The aforementioned photographs were taken in May 2021 from plants growing indoor in 12 cm pots in Andijk, The Netherlands. These plants were approximately 11 weeks of age.

The plant descriptions and measurements were taken in July 2023 in Enkhuizen, The Netherlands on outdoor plants grown in full soil. These plants were about 16 weeks old.

Color references are made to The Royal Horticultural Society Colour Chart (R.H.S.) 2001.

TABLE 1

DIFFERENCES BETWEEN THE NEW VARIETY 'PEHY0082' AND A SIMILAR VARIETY

| | 'PEHY0082' | Sanguna ® Sweet Pink, not patented |
|---|---|---|
| Earliness: | Medium early | Medium early |
| Flower size: | Very small | Medium to big |
| Branching: | Excellent branching | Medium branching |
| Foliage size: | Very small | Medium size |

Plant:

*Form, growth and habit.*—Semi trailing plant habit.
*Plant height.*—17 cm.
*Plant height (inflorescence included).*—21 cm.
*Plant diameter (width).*—Approximately 40 cm.

Roots:

*Number of days to initiate and produce roots.*—14 days at about 22° C.
*Type.*—Fine, fibrous, free branching.
*Color.*—RHS N158D.

Foliage:

*Arrangement.*—Alternate, simple; sometimes opposite, decussate.
*Immature leaf, color upper surface.*—RHS 137B.
*Immature leaf, color lower surface.*—RHS 137C.
*Mature leaf, color upper surface.*—RHS 137B.
*Mature leaf, color lower surface.*—RHS 137C.
*Length.*—1.5-2.5 cm.
*Width.*—0.6-0.8 cm.
*Shape.*—Ovate.
*Base shape.*—Acuminate.
*Apex shape.*—Acute.
*Margin.*—Entire.
*Texture, upper surface.*—Smooth, occasionally a short hair.
*Lower surface.*—Densely covered with short hairs.
*Color of veins, upper surface.*—RHS 138A.
*Color of veins, lower surface.*—RHS 138A.
*Petiole color.*—RHS 138A.
*Length.*—0.1 cm.
*Diameter.*—0.2 cm.
*Petiole texture.*—Densely covered with short hairs.

Stem:

*Quantity of main branches per plant.*—4-5.
*Color of stem.*—RHS 138A.
*Length of stem.*—19 cm.
*Diameter.*—0.3 cm.
*Length of internodes.*—0.9-1.8 cm.
*Texture.*—Dense, mostly glandular short hairs.
*Color of pedicel.*—RHS 138A.
*Length of pedicel.*—1.3-1.9 cm.
*Diameter of pedicel.*—0.2 cm.
*Texture of pedicel.*—Densely covered with short hairs.

Inflorescence:

*Type.*—Flowers solitary in upper leaf axis.
*Floret type.*—Funnel-shaped; 5 lobed petals; fused at base.
*Blooming habit.*—Medium early flowering in greenhouse, flowering throughout the summer months.
*Quantity of inflorescences per plant.*—Approximately 175.
*Lastingness of individual blooms on the plant.*—About 7 days.
*Fragrance.*—Rather strong smell.

Bud (just when opening):

*Color.*—RHS 56A at top, RHS 145C towards base.
*Length.*—2.0 cm.
*Width.*—0.4 cm.
*Shape.*—Oblong.

Immature inflorescence:

*Flower horizontal diameter.*—2.0 cm.
*Color petals, upper surface.*—RHS N74C.
*Color petals, lower surface.*—RHS 75D.

Mature flower:

*Flower horizontal diameter.*—2.4 cm.
*Flower height (vertical).*—3.0 cm.
*Color upper surface.*—RHS N74D with spots of RHS N74B, RHS 76D near throat.
*Color lower surface.*—RHS 75D.
*Conspicuousness of veins.*—Weak.
*Upper surface veins (yellowish primary veins).*—RHS 154A.
*Apex shape.*—Mostly rounded, occasionally a bit acuminate.
*Margin.*—Entire.
*Waviness of margin.*—Medium.
*Petal lobation.*—Medium to strong.
*Petal texture, upper surface.*—Smooth.
*Petal texture, lower surface.*—Smooth, occasionally a short hair mainly along veins.
*Corolla tube color outside.*—RHS 2C with veins RHS 145B.
*Corolla tube color inside.*—RHS 14C with veins RHS 1B at base, to RHS 17B at end of throat. (The inner veins look indeed darker than in reality, probably due to the fact that they are less exposed to light).
*Amount of the whitish area towards the base of the corolla.*—Small.

*Conspicuousness of veins in tube*.—Medium.
*Corolla tube length*.—1.3 cm.
*Corolla tube texture, outside*.—Dense and short glandular hairs.
*Corolla tube texture, inside*.—Glabrous.

Calyx:
*Color of sepal, upper surface*.—RHS 137B.
*Color of sepal, lower surface*.—RHS 137C.
*Length*.—0.6 cm.
*Width*.—0.1 cm.
*Shape*.—Ensiform.
*Apex shape*.—Acute.
*Base*.—Fused.
*Margins*.—Entire.
*Texture, upper surface*.—Densely covered with short glandular hairs.
*Lower surface*.—Densely covered with short glandular hairs.

Reproductive organs:
*Pistil*.—1.
*Length*.—1.7 cm.
*Style color*.—RHS 145D.
*Style length*.—1.4 cm.
*Stigma color*.—RHS 14A.
*Stamens*.—
*Quantity per flower*.—5.
*Color of filaments*.—RHS 157D.
*Length filaments*.—1.4 cm.
*Anther color*.—RHS 155D.
*Anther length*.—0.2 cm.
*Anther shape*.—Elliptical.
*Color of pollen*.—RHS 158C.
*Pollen amount*.—Abundant.
*Fertility/seed set*.—Has not been observed on this hybrid.
*Disease/pest resistance*.—Has not been observed on this hybrid.

What is claimed is:

1. A new and distinct variety of *Petunia* plant named 'PEHY0082' substantially as illustrated and described herein.

* * * * *